United States Patent
Strickland et al.

(10) Patent No.: US 12,357,421 B2
(45) Date of Patent: Jul. 15, 2025

(54) BRUSHING DEVICE FOR CLEANING ENDOTRACHEAL TUBES

(71) Applicants: Ashley Strickland, Beech Island, SC (US); Michael W. Quinn, Beech Island, SC (US)

(72) Inventors: Ashley Strickland, Beech Island, SC (US); Michael W. Quinn, Beech Island, SC (US)

(*) Notice: Subject to any disclaimer, the term of this patent is extended or adjusted under 35 U.S.C. 154(b) by 0 days.

(21) Appl. No.: 18/134,275

(22) Filed: Apr. 13, 2023

(65) Prior Publication Data

US 2024/0341913 A1    Oct. 17, 2024

(51) Int. Cl.
*A61B 90/70* (2016.01)
*A46B 15/00* (2006.01)
*A61M 16/04* (2006.01)

(52) U.S. Cl.
CPC .......... *A61B 90/70* (2016.02); *A46B 15/0055* (2013.01); *A61M 16/04* (2013.01); *A61B 2090/701* (2016.02)

(58) Field of Classification Search
CPC ..... A61B 90/70; A46B 15/0055; A61M 16/04
See application file for complete search history.

(56) References Cited

U.S. PATENT DOCUMENTS

| | | | | |
|---|---|---|---|---|
| 5,003,657 A | * | 4/1991 | Boiteau | B08B 9/0436 |
| | | | | 15/104.18 |
| 6,082,361 A | * | 7/2000 | Morejon | A61M 16/0463 |
| | | | | 128/207.14 |
| 2006/0191087 A1 | * | 8/2006 | Maguire | A61B 90/70 |
| | | | | 15/104.16 |
| 2011/0023887 A1 | * | 2/2011 | Vazales | A61B 1/267 |
| | | | | 128/207.29 |

FOREIGN PATENT DOCUMENTS

| | | |
|---|---|---|
| CN | 105124912 | 12/2015 |
| CN | 205379284 | 7/2016 |
| CN | 107028583 | 8/2017 |
| CN | 206403422 | 8/2017 |
| CN | 208435608 | 1/2019 |
| CN | 209284459 | 8/2019 |
| CN | 112933312 | 6/2021 |

OTHER PUBLICATIONS

Cacau, Santana-Filho, Carvalho, Endotracheal Tube Cleaning With a Novel Mechanism for Secretion Removal, Editorial, Respiratory Care, Nov. 2016, 61 (11) 1560-1561; DOI: https://doi.org/10.4187/respcare.05216.
Instructions for Use, endOclear Liberator CS, Closed Suction System for Adults (2017).

* cited by examiner

*Primary Examiner* — Erin F Bergner (74) *Attorney, Agent, or Firm* — B. Craig Killough (57) ABSTRACT

A device and method for cleaning endotracheal tubes in situ. A brush is positioned near a distal end of a linkage the traverses the lumen of the tube. When a handle, the linkage and the brush are in a retracted position, the brush is constrained within the lumen of the tube. When the handle is advanced to push the brush and as stopper out of the distal end of the lumen of the tube, the brush and stopper expand sufficiently to contact an interior a lumen of an endotracheal tube and the stopper seals liquids from escaping the ET tube. As the device is withdrawn from the ET tube, the brush scrubs the sides of the ET tube, and the stopper prevents the liquid from escaping from the ET tube and into the patient.

15 Claims, 11 Drawing Sheets

BRUSHING DEVICE FOR CLEANING ENDOTRACHEAL TUBES

BACKGROUND OF THE INVENTION

Intubation involves the insertion of a tube either through the mouth or nose and into the airway to aid breathing, deliver anesthesia or medications, and bypass a blockage. It is called endotracheal intubation when the tube is inserted into the mouth. The tube that is inserted into the mouth and airway is called an endotracheal tube, which is referred to herein as an "ET tube." In some cases, the ET tube is surgically placed into the trachea.

ET tubes are flexible plastic tubes that have a lumen. Most modern endotracheal tubes today are constructed of polyvinyl chloride. Tubes constructed of silicone rubber, wire-reinforced silicone rubber or stainless steel are also available. For human use, ET tubes typically range in size from 2 to 10.5 mm (0.1 to 0.4 in) in internal diameter.

Placement of an ET tube is an invasive and uncomfortable medical procedure. Therefore, intubation usually involves administration of general anesthesia and a neuromuscular-blocking drug. Placement of the ET tube is facilitated by using a conventional laryngoscope, flexible fiberoptic bronchoscope, or video laryngoscope.

Biofilms develop in ET tubes. Biofilms harbor potentially harmful pathogens. Multiple factors contribute to the development of biofilms, but secretions into the ET tube is a primary factor. The quantity of biofilms, secretions, and associated pathogens increases as the service life of the ET tube increases.

Replacing the ET tube after a period of time removes the pathogens associated with the ET tube. However, replacement of the ET tube is uncomfortable for the patient and creates risks to the patient. Risks associated with general anesthesia are present. Patients who are intubated are frequently palliative or otherwise have serious medical conditions that discourage procedures such as replacement of ET tubes unless necessary. Improper placement of an ET tube can damage tissue, or result in inadequate oxygen to the patient, leading to brain damage or death.

There is a need for a device and process that will extend the service life of ET tubes.

SUMMARY OF THE INVENTION

The present invention is a device for cleaning endotracheal tubes in situ. A method of using the device for cleaning endotracheal tubes in situ is also described. The device has a tube comprising a lumen. A linkage is present within the tube. A handle is positioned near a proximal end of the linkage for manipulating the linkage. A brush is positioned near a distal end of the linkage that traverses a distal portion of the lumen of the tube. The linkage traverses the lumen of the tube and connects the handle and the brush.

When the handle, and therefore the linkage and the brush, are in a retracted position, the brush is constrained within the lumen of the tube. When the handle is advanced to push the brush out of the distal end of the lumen of the tube, the brush expands sufficiently to contact an interior circumference of a lumen of an endotracheal tube.

The device for cleaning endotracheal tubes preferably has a stopper near the distal end of the linkage and a second stopper near a proximal end of the linkage and distal to the handle. When the handle is in the retracted position, the stopper is constrained within the lumen of the tube. When the handle is advanced to push the stopper out of the distal end of the lumen of the tube, the brush expands sufficiently to contact an interior circumference of a lumen of an ET tube and seal liquids from escaping the ET tube. Ports in the lumen of the tube allow saline or other cleaning liquids to be introduced into the lumen of the tube and the ET tube. The second stopper prevents liquids from escaping from the proximal end of the lumen of the tube. As the device is withdrawn from the ET tube, the brush scrubs the sides of the ET tube, and the stopper prevents the liquid from escaping from the ET tube and into the patient.

DESCRIPTION OF PREFERRED EMBODIMENTS

The present invention is a device for cleaning endotracheal tubes in situ, that is, with the ET tube in position in the trachea of the patient, without the necessity of moving or removing the ET tube from the patient. The device permits flushing of the ET tube, such as with saline, and uses a brush to scrub the interior surfaces of the lumen of the ET tube.

Debris, biological materials and associated pathogens can be removed to extend the service life of the ET life. The device of the invention is preferred to be used with a flexible bronchoscope for proper positioning of the device.

An ET tube 2 as contemplated herein is a flexible plastic tube having a lumen. The ET tube is characterized by a proximal opening and a distal opening. An inflatable cuff 22 holds the ET tube in place within the airway of the patient. The proximal end of the ET tube may communicate with a ventilator or other oxygen supply.

In a preferred embodiment, the device for cleaning an ET tube comprises a tube 4 comprising a lumen. The outside diameter of the tube fits with the instrument channel 24 and the insertion tube 20 of the bronchoscope. A linkage 8 is present within the tube. A handle 12 is positioned near a proximal end of the linkage construct for advancing and retracting the linkage. A brush 6 is positioned near a distal end of the linkage traverses a distal portion the lumen of the tube. Linkage 8 traverses the lumen of the tube and connects the handle and the brush, so that movement of the handle advances the brush out of the lumen of tube 4.

Figures 8, 9:
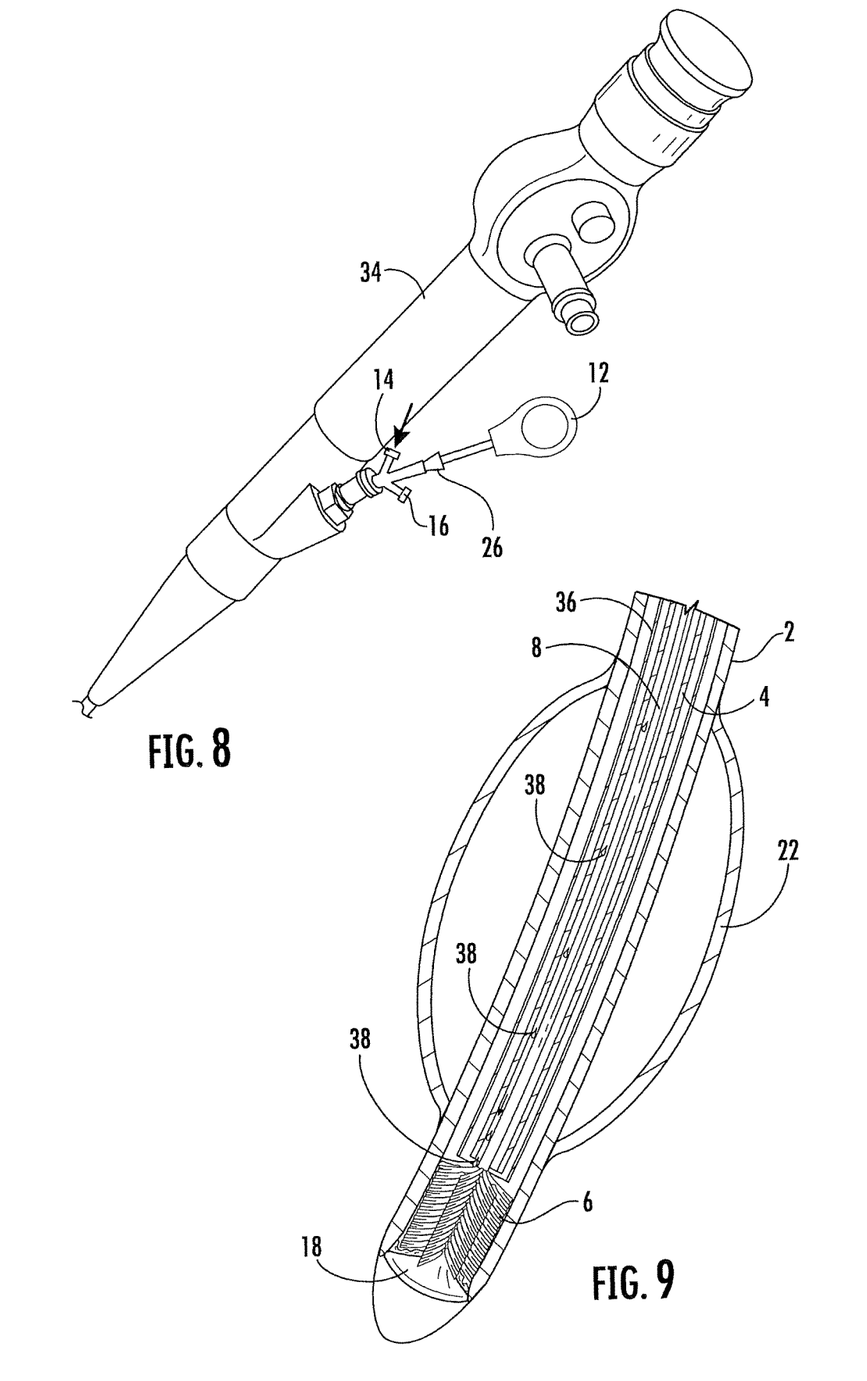
FIG. 8 is an enlarged perspective view of the bronchoscope with the ET tube cleaning device advanced as in FIG. 6 and FIG. 7, showing the ports of the ET tube cleaning device for insertion and suctioning cleaning liquid into the device and the ET tube.
FIG. 9 is an enlarged isolation taken from line 9-9 of FIG. 7 and showing the ET tube, ET tube cleaning device and the insertion tube of the bronchoscope sectioned, and showing the brush and stopper advanced from the lumen of the ET tube cleaning device and in contact with the interior surfaces of the ET tube.

Preferably the device according to the invention provides a port 14 for inserting a cleaning liquid, such as saline or other non-toxic cleaning liquids, and a port 16 for suctioning the liquid from the port. When brush 6 is advanced out of the lumen of the tube, the cleaning liquid 36 can enter the ET tube. FIG. 9.

The use of the cleaning liquid means that the distal end of the ET tube 2 must be sealed sufficiently to prevent harmful quantities of the cleaning liquid from entering the patient's airway. A stopper 18 is provided that is distal to the brush. The stopper is formed of an elastomeric or similarly flexible material that provides a seal at the distal end of the ET tube. The stopper may have a conical shape with the taper enlarging toward the lower portion of the stopper. This shape facilitates removal of the device as the device traverses the ET tube. The shape may be similar to the head of suction cup style darts, but small enough to fit within the lumen of the ET tube cleaning device and large enough when expanded to seal the ET tube.

A second stopper 26 is present at the proximal end of the linkage and distal to the handle. The second stopper closes the proximal opening of the tube of the device to retard the cleaning liquid from exiting the tube 4 of the device through the proximal opening. The second stopper may be formed of an elastomeric material that promotes closing of the opening to the tube.

Figure 4:
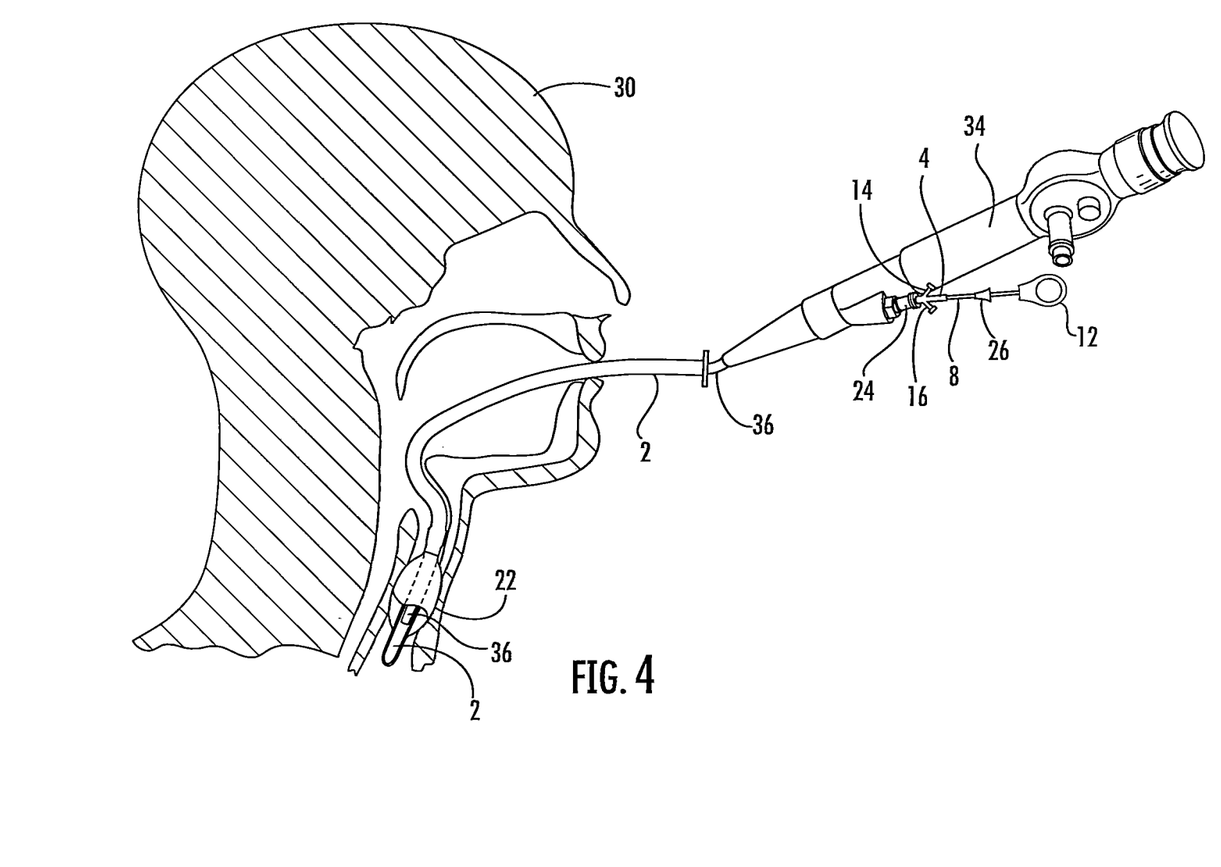
FIG. 4 shows the elements of FIG. 3, with the ET tube cleaning device of the invention fully inserted into the port of the bronchoscope and positioned in the ET tube with the aid of the bronchoscope.
Figure 5:
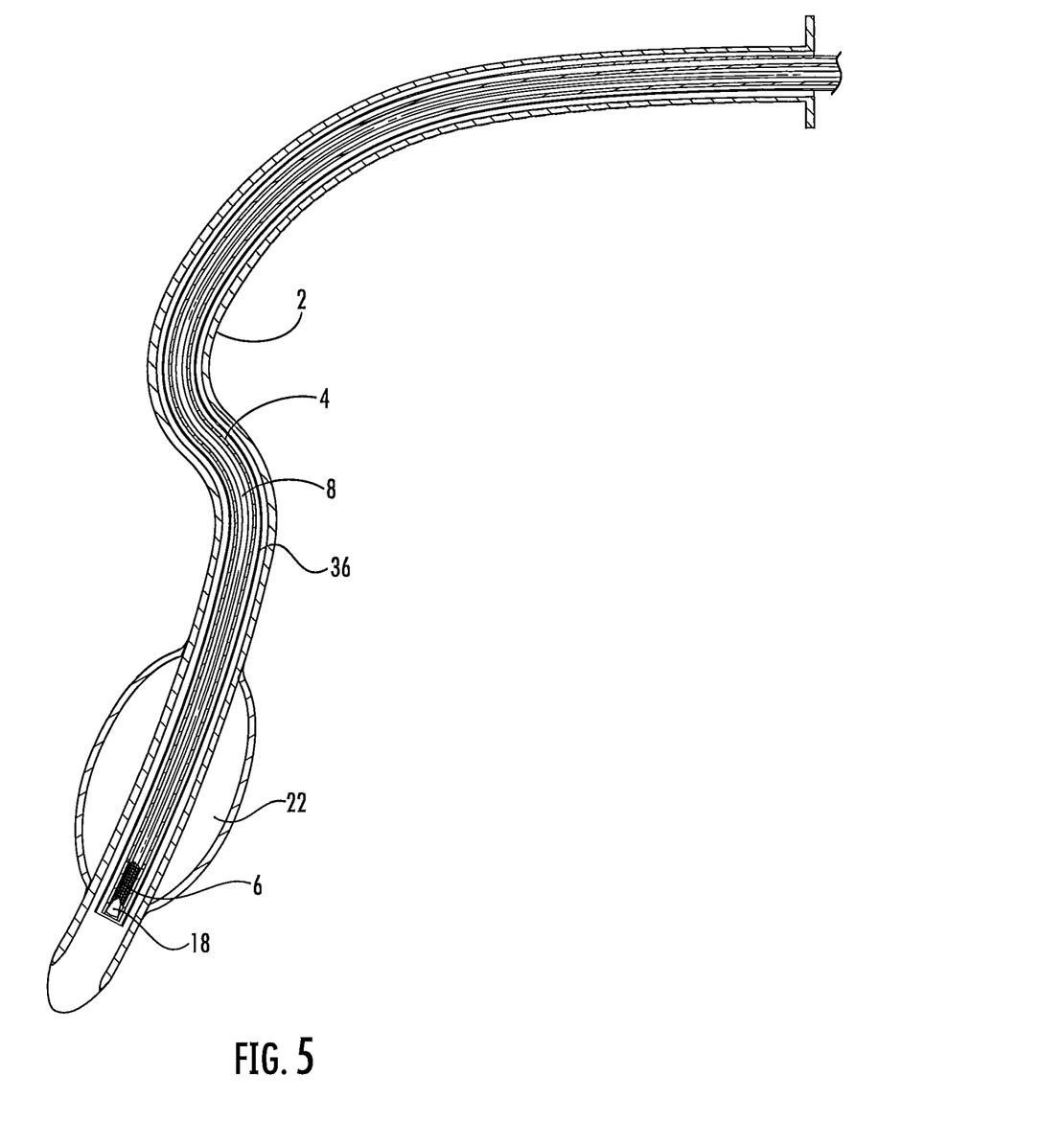
FIG. 5 shows the side, sectioned ET tube of FIG. 2, with a side, sectioned view of the insertion tube of the bronchoscope and a side, sectioned view of the ET tube cleaning device of the invention present and positioned in the bronchoscope.
Figure 6:
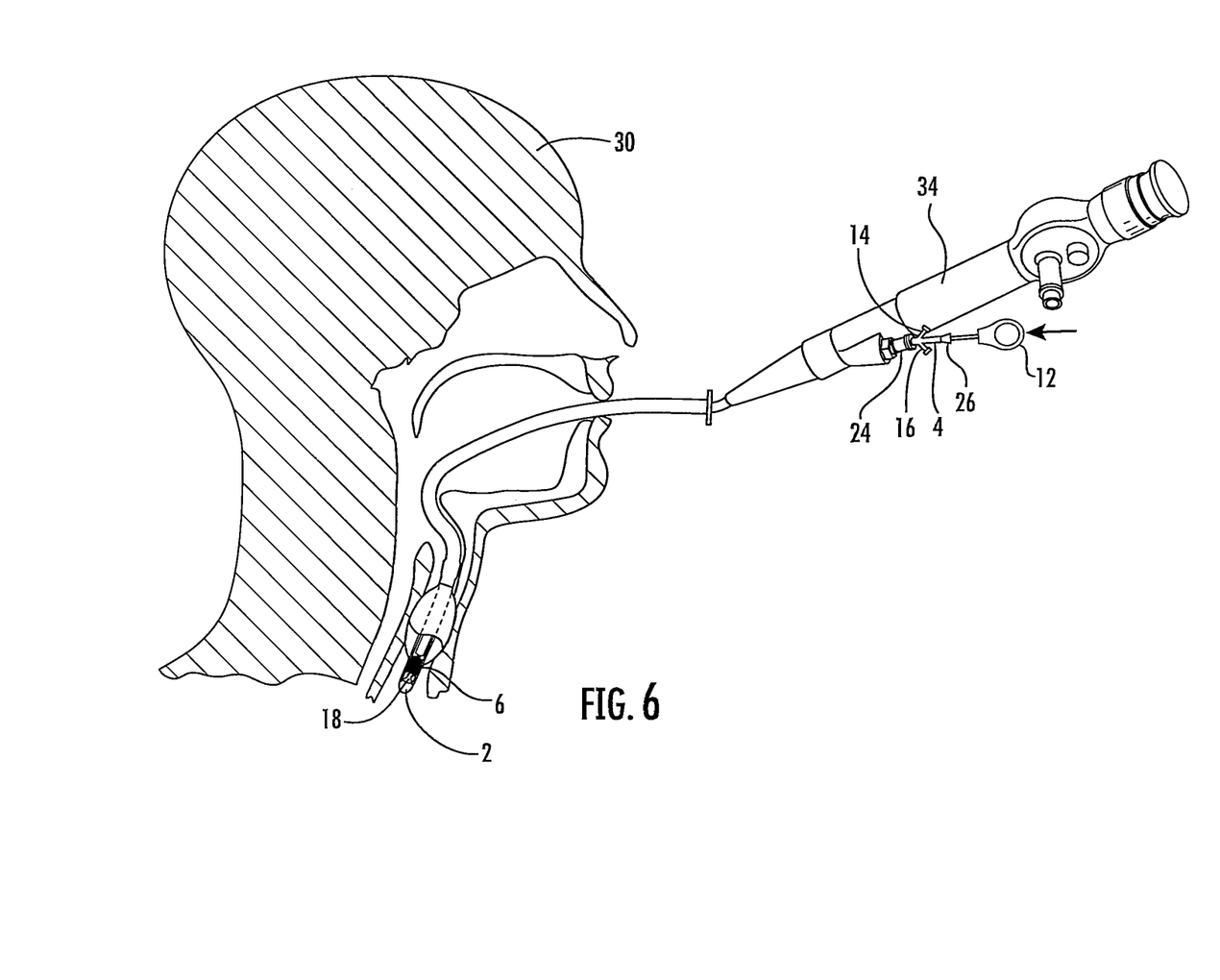
FIG. 6 shows the construct of FIG. 4, with the handle of the ET tube cleaning device of the invention advanced so that the linkage pushes the brush and stopper from the lumen of the cleaning device.
Figure 7:
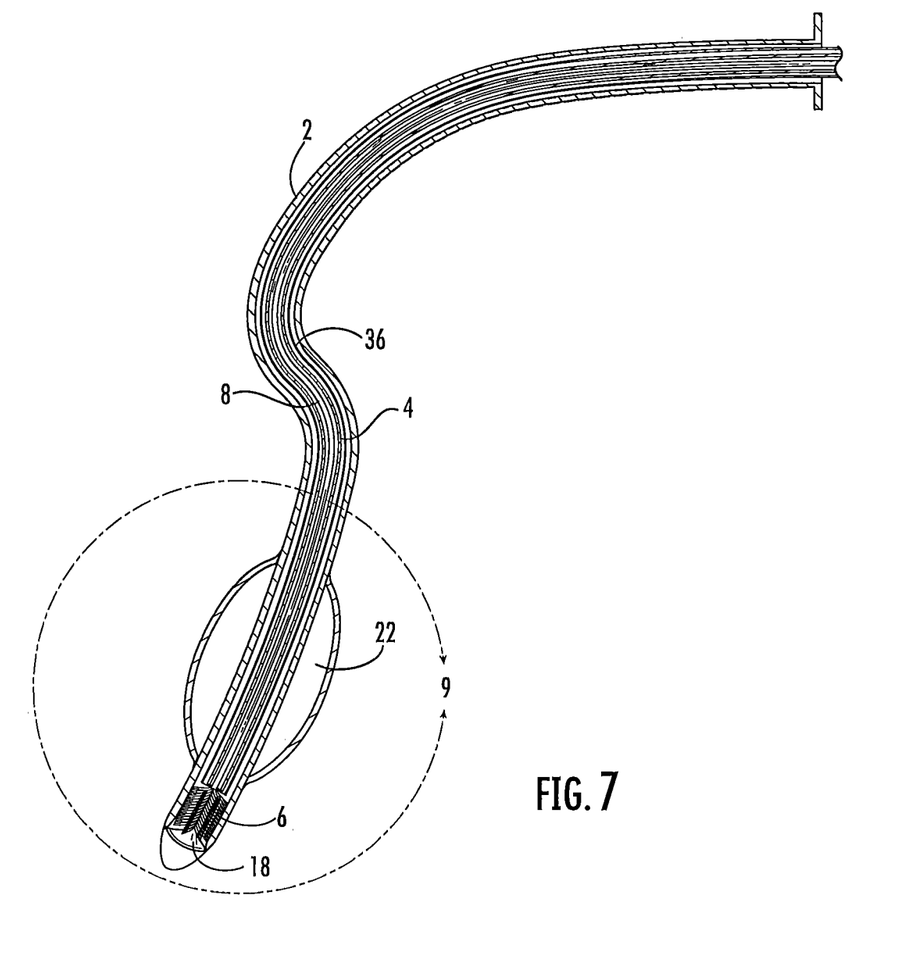
FIG. 7 shows the construct of FIG. 5, with the handle of the ET tube cleaning device of the invention advanced so that the linkage pushes the brush and stopper from the lumen of the cleaning device.

When inserted into the bronchoscope port 24, linkage 8 is retracted with the handle 12 and second stopper 26 spaced apart from the proximal opening of tube 4. FIG. 4. The brush 6 and the stopper 18 are contained and restrained at a distal end of the lumen of the tube 4 and are within the tube. The brush and the stopper 18 are not in contact with the ET tube when the handle and linkage are in this retracted position. FIG. 5. After positioning the ET tube cleaning device in the ET tube 2, the linkage is advanced using the handle. FIG. 6. The brush and the stopper 18 expand after they are no longer constrained by the tube 4. The stopper 18 seals the distal end of the ET tube 2, and the second stopper 26 closes the opening to the tube 4 of the ET tube cleaning device. Linkage 8 is longer than tube 4 that it traverses, so that the brush and stopper exit the tube when the linkage is fully advanced to push the brush and stopper from the distal end of the tube. The brush and stopper expand. FIG. 7. The distal opening of tube 4 also communicates with the ET tube 2 to allow cleaning liquid to enter the ET tube.

The brush and the stopper must be sized to fit within the lumen of the tube 4, and sufficiently resilient to unfold and contact the circumference of the interior surface of the ET tube when advanced out of the lumen of the tube. FIG. 9.

Figure 1:
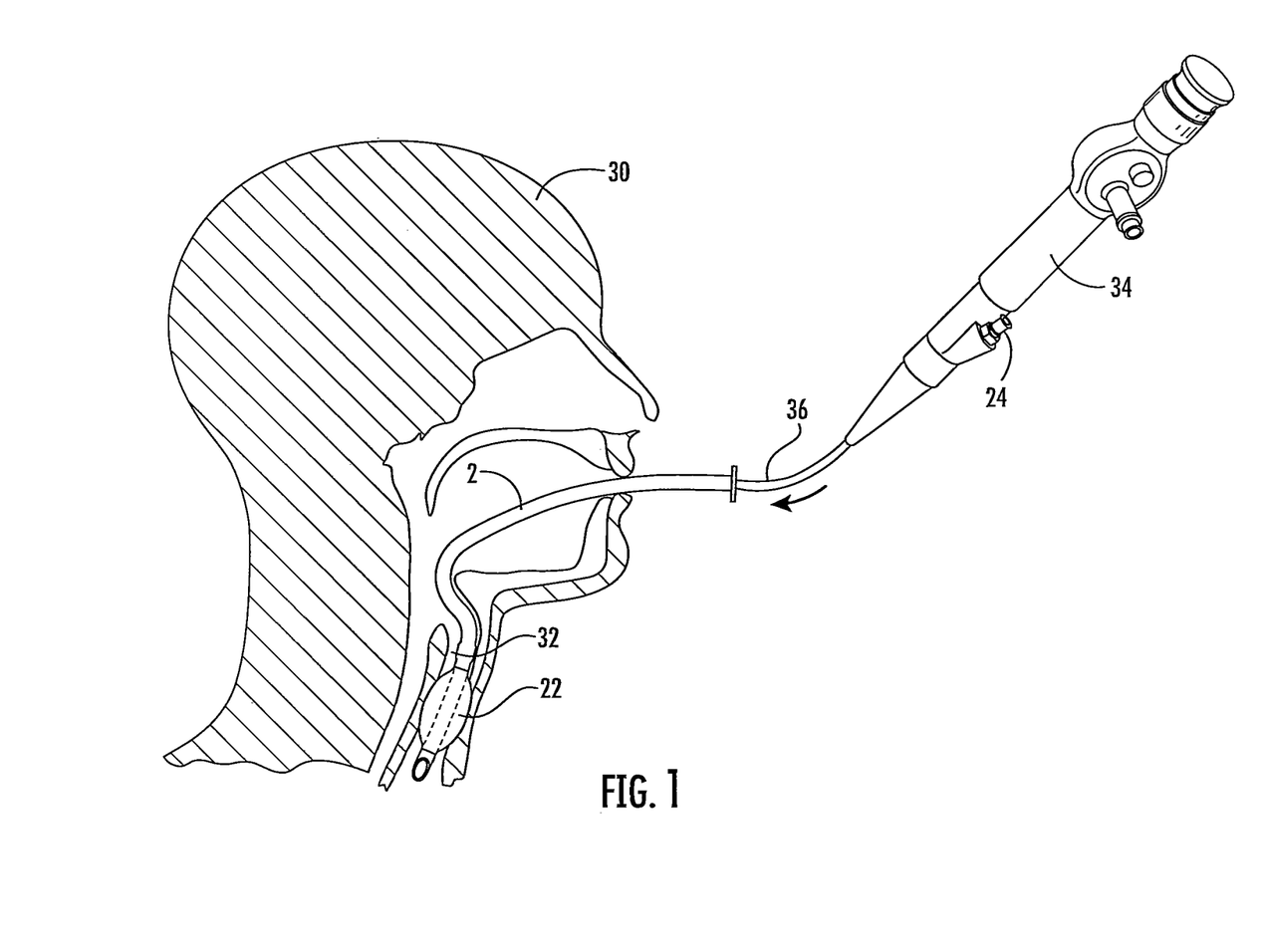
FIG. 1 demonstrates a bronchoscope insertion tube inserted into an ET tube.
Figure 2:
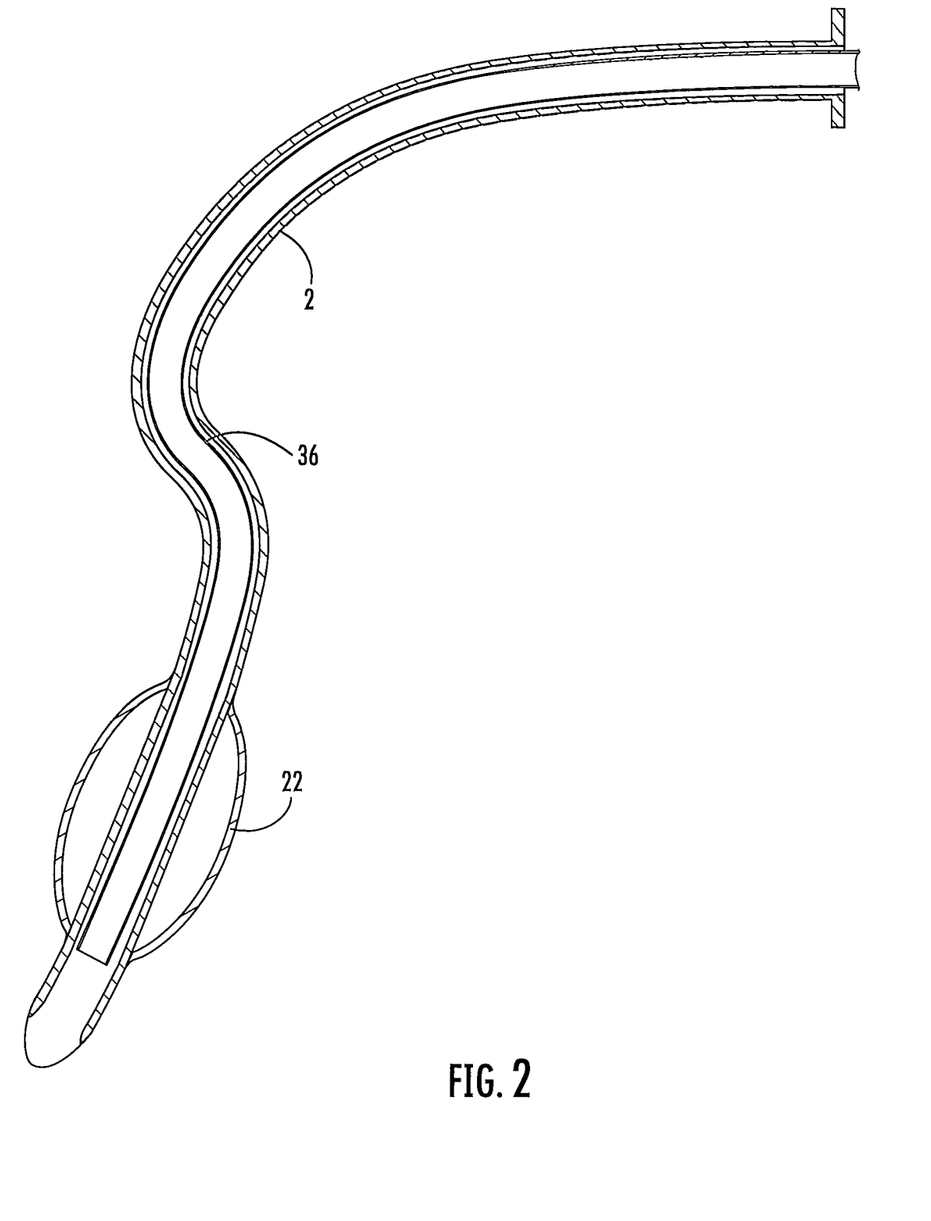
FIG. 2 shows a side, sectioned ET tube.
Figure 3:
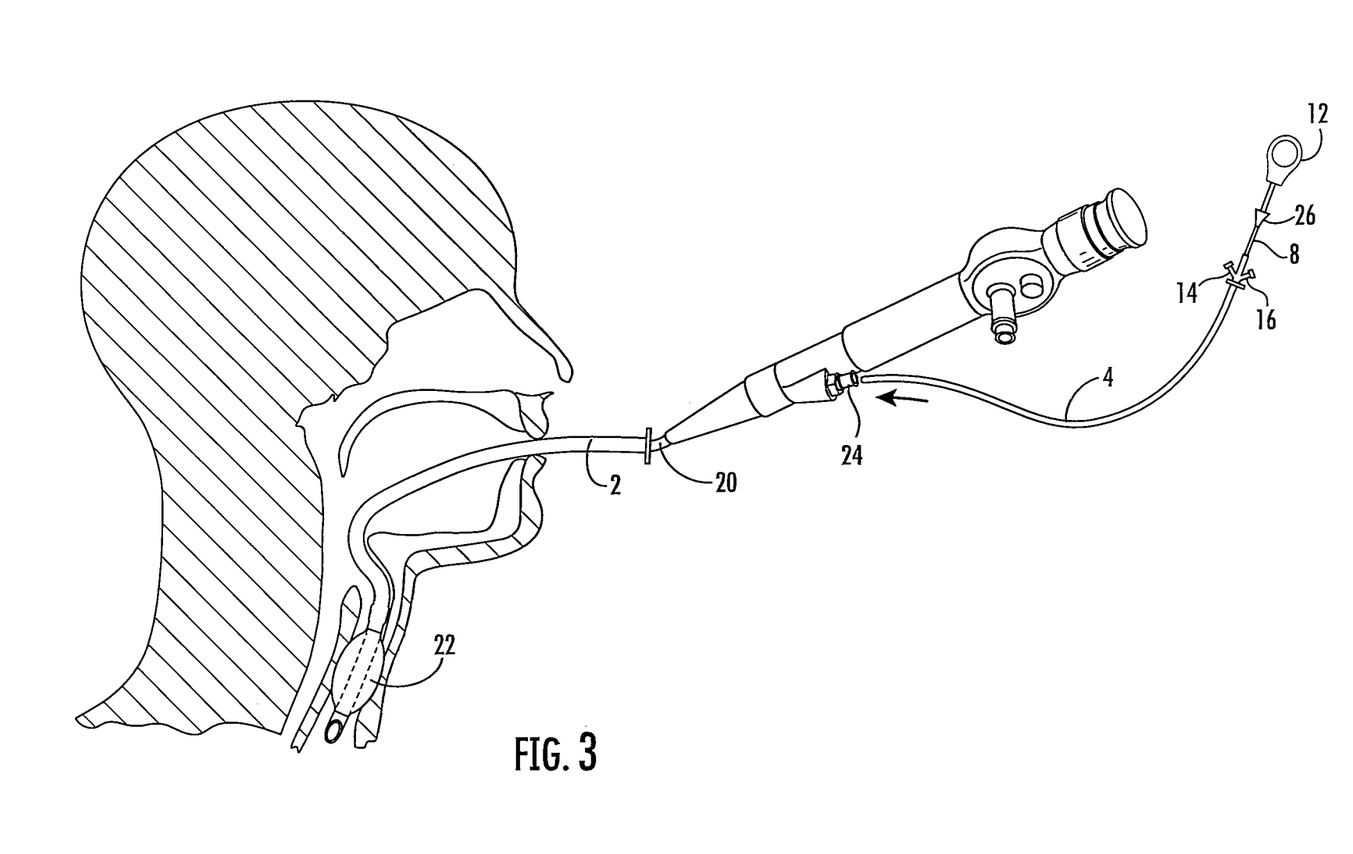
FIG. 3 shows the bronchoscope of FIG. 1 inserted into an ET tube, with the ET tube cleaning device of the invention ready for insertion into a port of the bronchoscope.

In use, a patient 30 has an ET tube 2 inserted through the mouth and positioned in the trachea 32. The ET tube is held in place by a cuff 22 that prevents air leaks and holds the ET tube in place, although some ET tubes do not have cuffs. FIG. 1. Insertion tube 36 of a bronchoscope 34 is inserted into the ET tube 2 with a distal end of the insertion tube finally positioned near the distal end of the ET tube. Next, the tube of the device is inserted into port 24 of the bronchoscope and through the insertion channel of the bronchoscope and the insertion tube of the bronchoscope. FIG. 3; FIG. 4. The bronchoscope is used to finely position the device, so that the distal end of the tube 4 is near the distal end of the ET tube to clean substantially the entire length of the ET tube, but the stopper 18 and brush 6 do not extend out of the distal end of the ET tube. FIG. 5.

After the ET tube cleaning device is positioned, the handle 12 is advanced to push the stopper 18 and the brush 6 out of the lumen of the tube, while the stopper and brush remain within the ET tube. The brush and the stopper must be formed so as the be compressed within the lumen of the tube when the construct is retracted (FIG. 5), but expand so as to contact the interior surfaces of the circumference of the ET tube when the brush and stopper are advanced out of tube 4 (FIG. 7; FIG. 8; FIG. 9).

The stopper 18 seals the distal end portion of the ET tube 2. Cleaning liquid, such as saline, may be inserted into the lumen of tube 4 through a port, such as port 14. In one example, 6-12 cc of cleaning liquid is inserted in a port in tube 4, although the amount of cleaning liquid is dependent on the size of the ET tube and condition of the ET tube. A larger or more fouled ET tube may require additional cleaning liquid and suctioning. The second port 16 may be used to suction the cleaning liquid from the ET tube 2 and tube 4. A portion of the cleaning liquid may be left in the ET tube to assist loosening and brushing material from the ET tube as tube 4 is withdrawn from the ET tube 2.

As the handle 12 and linkage 8 are advanced and the stopper 18 and brush 6 exit the lumen of the tube 4, the second stopper 26 seals the proximal opening of the lumen of the tube 4. The second stopper also acts as a stop to limit the travel of the stopper and the brush. When the stopper and the brush have exited the lumen of the tube 4, the tube 4 opens into the ET tube 2 so that cleaning liquid 36 flows into the ET tube. FIG. 9. The cleaning liquid is prevented from exiting the distal end of the ET tube by the stopper 18.

Figure 10:
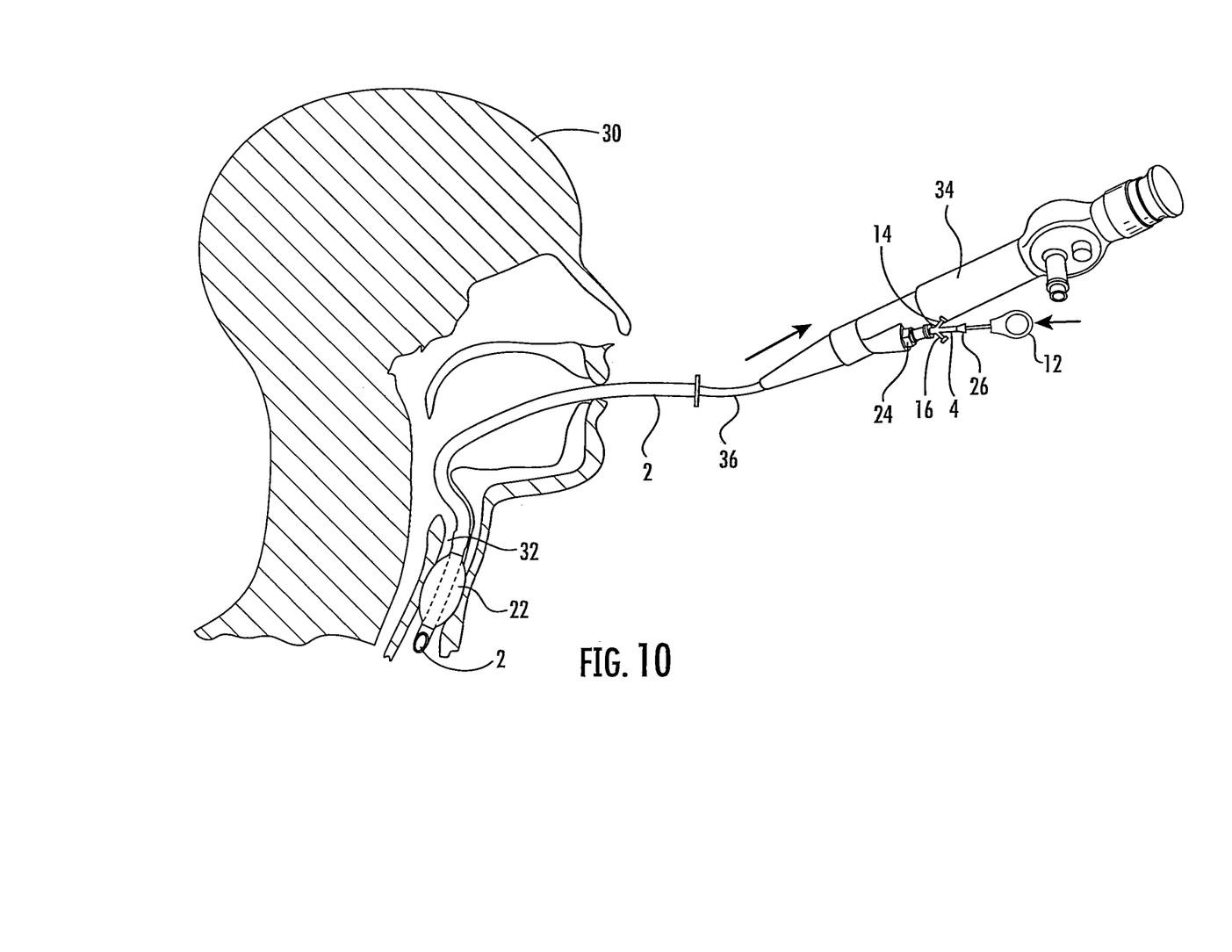
FIG. 10 demonstrates the withdrawal of the ET tube cleaning device and bronchoscope from the ET tube while the ET tube remains in place.
Figure 11:
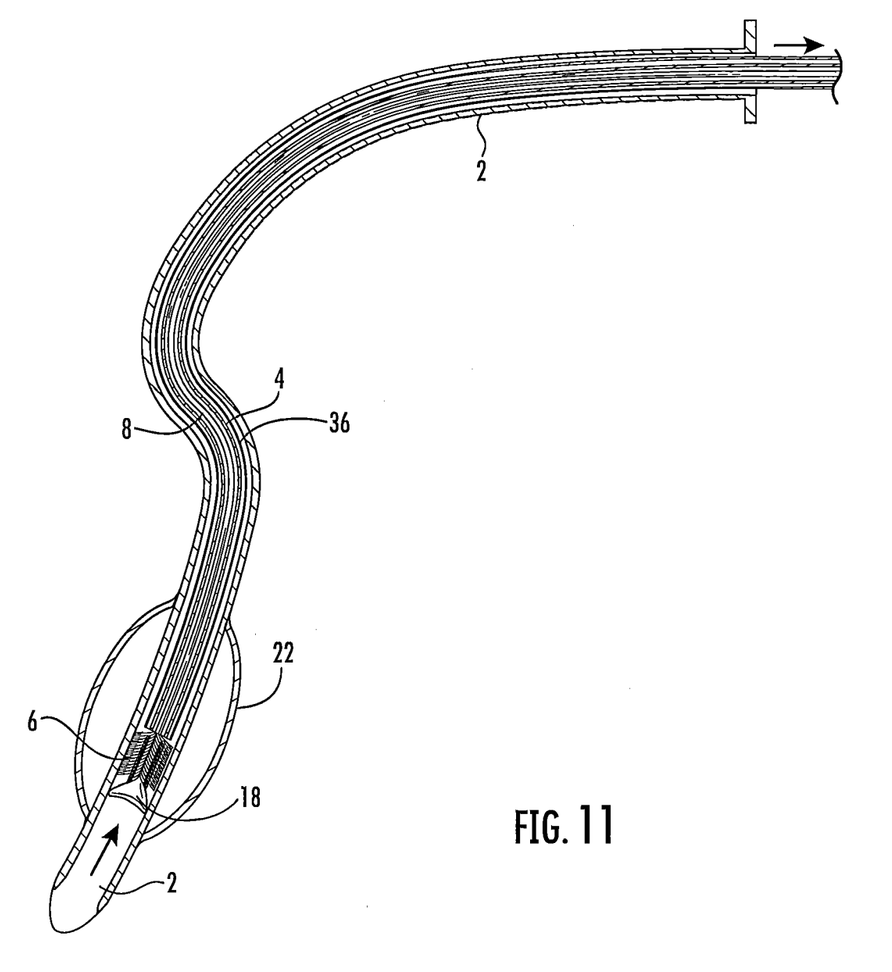
FIG. 11 shows the construct of FIG. 7, demonstrating withdrawal of the ET tube cleaning device and bronchoscope from the ET tube while the ET tube remains in place.
Figure 12:
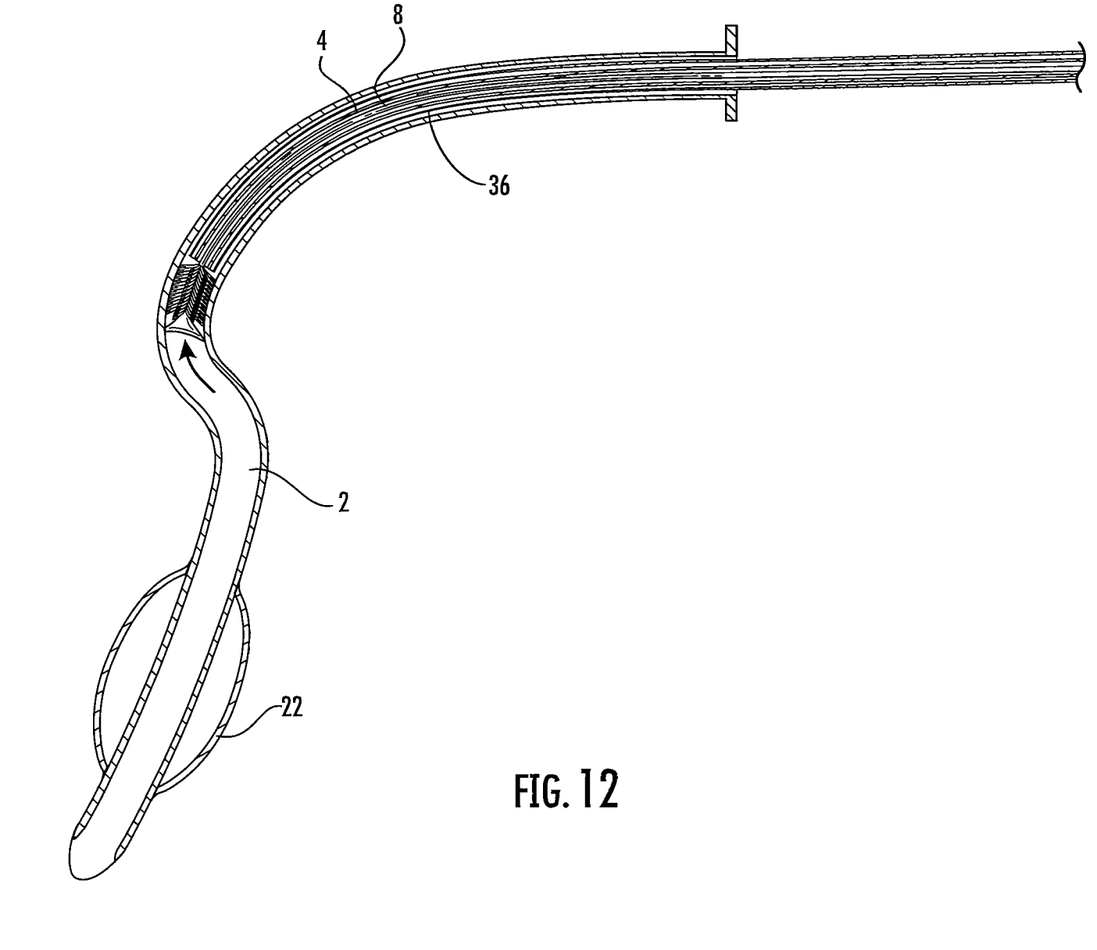
FIG. 12 shows the construct of FIG. 11, demonstrating further progressive withdrawal of the ET tube cleaning device and bronchoscope from the ET tube while the ET tube remains in place.

After a majority of the cleaning liquid is suctioned from the ET tube 2, the bronchoscope 34 and the ET tube cleaning device are withdrawn from the ET tube so as to not disturb positioning of the ET tube. FIG. 10. As the ET tube cleaning device is withdrawn, brush 6 scrubs the surfaces of the interior of the lumen of the ET tube, with debris on the lumen surfaces of the ET tube having been softened or disturbed by the cleaning liquid. FIG. 10; FIG. 11. The cleaning liquid may contain agents that kill pathogens and retard pathogen growth. The debris and biofilm scrubbed from the ET tube is pulled out, with the resilient stopper acting as a squeegee to assist in removing liquid and debris from the ET tube.

After the ET tube cleaning device is removed from the ET tube 2 and the bronchoscope 34, the bronchoscope may be reinserted into the ET tube without the cleaning device of the invention to inspect the ET tube. If debris or biofilm remains, the process may be repeated, specifically targeting any areas of the ET tube where debris or biofilm is observed.

The device and method clean the interior surfaces of the lumen of the ET tube. The service life of the ET tube is extended, or the need for replacement is resolved, thereby reducing patient risk of the procedure and the expense and discomfort associated with replacement of the ET tube.

What is claimed:

1. A device for cleaning an endotracheal tube, comprising:
   a tube comprising a lumen, wherein the tube comprises a first port that extends from a side of the tube and communicates with the lumen of the tube and wherein the first port is constructed and arranged to receive cleaning liquid therein, and a second port that extends from the side of the tube and communicates with the lumen of the tube, and wherein the second port is constructed and arranged to suction cleaning liquid from the tube, and the tube comprises an opening at a distal end of the tube;
   a plunger, the plunger comprising:
   a handle positioned near a proximal end of the plunger;
   a brush positioned near a distal end of the plunger that traverses the lumen of the tube;
   a linkage that extends into the lumen of the tube at an opening in a proximal end of the lumen of the tube and traverses the lumen of the tube and connects the handle and the brush, wherein a length of the linkage from the handle to the brush exceeds the length of the tube;
   a sealing stopper positioned distal to the brush, the sealing stopper collapsed when positioned inside the tube and constructed and arranged to expand when out of the opening at the distal end of the tube, the expanded sealing stopper constructed and arranged to contact an interior circumference of an endotracheal tube and form a liquid seal in the endotracheal tube by expansion that seals the liquid cleaning material from escaping the interior of the endotracheal tube;
   a second stopper positioned on the linkage is constructed and arranged to be selectively spaced apart from or positioned within an opening in the proximal end of the lumen of the tube to form a seal in the opening in the proximal end of the tube;
   wherein, when the handle is in a retracted position, the brush is constrained within the lumen of the tube, and when the handle is moved to an advanced position, the linkage pushes the brush out of the distal end of the lumen of the tube, and the brush is constructed and arranged to expand and to contact an interior circumference of the endotracheal tube.

2. A device for cleaning an endotracheal tube as described in claim 1, wherein the distal end of the lumen of the tube opens into and is in liquid communication with a lumen of the endotracheal tube when the handle is moved to an advanced position and the brush is out of the lumen of the tube.

3. A device for cleaning an endotracheal tube as described in claim 1, wherein the first port and the second port are in liquid communication with the lumen of the tube, and the first port is constructed and arranged to allow the cleaning liquid to flow into the lumen of the tube, and wherein the distal end of the lumen of the tube opens into and is in liquid communication with a lumen of an endotracheal tube when the handle is moved to an advanced position and the linkage pushes the brush out of the distal end of the lumen of the tube.

4. A device for cleaning an endotracheal tube as described in claim 1, further comprising a bronchoscope, where in the tube and the plunger are constructed and arranged for insertion inserted through a port and lumen of the bronchoscope and the bronchoscope depicts a location of the distal end of the tube.

5. A method of cleaning an endotracheal tube using the device for cleaning an endotracheal tube as described in claim 1, comprising the steps of:
   inserting the tube and plunger into an endotracheal tube,
   advancing the handle and linkage and moving the brush out of the tube so that the brush expands;
   withdrawing the tube and plunger from the endotracheal tube so that the brush contacts interior surfaces of the endotracheal tube.

6. A method of cleaning an endotracheal tube using the device for cleaning an endotracheal tube as described in claim 1, comprising the steps of:
   inserting the tube and plunger into an endotracheal tube,
   advancing the handle and linkage and moving the brush and stopper out of the tube so that the stopper and brush expand;
   placing a cleaning liquid into the endotracheal tube, wherein the stopper seals the endotracheal tube
   withdrawing the tube and plunger from the endotracheal tube so that the brush contacts interior surfaces of the endotracheal tube.

7. A method of cleaning an endotracheal tube using the device for cleaning an endotracheal tube as described in claim 6, further comprising the step of:
   suctioning the cleaning liquid from the endotracheal tube prior to withdrawing the tube and plunger from the endotracheal tube.

8. A method of cleaning an endotracheal tube using the device for cleaning an endotracheal tube as described in claim 5, further comprising the step of:
   positioning the tube and plunger in the endotracheal tube with a bronchoscope.

9. A method of cleaning an endotracheal tube using the device for cleaning an endotracheal tube as described in claim 6, further comprising the step of:
   positioning the tube and plunger in the endotracheal tube with a bronchoscope.

10. A device for cleaning an endotracheal tube as described in claim 1, wherein the stopper is formed in a generally conical shape with the taper of the generally conical shape enlarging toward the distal end of the stopper.

11. A device for cleaning an endotracheal tube, comprising:
    a tube comprising a lumen, wherein the tube comprises a first port that extends from a side of the tube and communicates with the lumen of the tube and wherein the port is constructed and arranged to receive cleaning liquid therein, and the tube comprises an opening at a distal end of the tube;
    a plunger, the plunger comprising:
    a handle positioned near a proximal end of the plunger;
    a brush positioned near a distal end of the plunger that traverses the lumen of the tube;
    a linkage that extends into the lumen of the tube at an opening in a proximal end of the lumen of the tube and traverses the lumen of the tube and connects the handle and the brush;
    a sealing stopper positioned distal to the brush, the sealing stopper collapsed when positioned inside the tube and constructed and arranged to expand when out of the tube, the expanded sealing stopper constructed and arranged to contact an interior circumference of an endotracheal tube and form a liquid seal in the endotracheal tube by expansion that seals the liquid cleaning material from escaping the interior of the endotracheal tube;

a second stopper positioned on the linkage is constructed and arranged to be positioned within an opening in the proximal end of the lumen of the tube;

wherein, when the handle is in a retracted position, the brush is constrained within the lumen of the tube, and when the handle is moved to an advanced position, the brush is out of the distal end of the lumen of the tube, and the brush is constructed and arranged to expand and expands sufficiently to contact an interior circumference of the endotracheal tube.

12. A device for cleaning an endotracheal tube as described in claim 11, wherein the stopper is formed in a generally conical shape with a taper of the generally conical shape enlarging toward the distal end of the stopper.

13. A device for cleaning an endotracheal tube as described in claim 11, wherein the distal end of the lumen of the tube opens into and is in liquid communication with a lumen of the endotracheal tube when the handle is moved to the advanced position and the brush is out of the lumen of the tube.

14. A device for cleaning an endotracheal tube as described in claim 11, wherein the first port is in liquid communication with the lumen of the tube, and the first port is constructed and arranged to allow the cleaning liquid to flow into the lumen of the tube, and wherein the distal end of the lumen of the tube opens into and is in liquid communication with a lumen of an endotracheal tube when the handle is moved to the advanced position and the linkage pushes the brush out of the distal end of the lumen of the tube.

15. A device for cleaning an endotracheal tube as described in claim 11, further comprising a bronchoscope, where in the tube and the plunger are constructed and arranged for insertion inserted through a port and lumen of the bronchoscope and the bronchoscope depicts a location of the distal end of the tube.

\* \* \* \* \*